United States Patent [19]

LeVeen et al.

[11] 4,369,789

[45] Jan. 25, 1983

[54] INFLATABLE GASTRIC FEEDING TUBE

[76] Inventors: Eric G. LeVeen, 3-3 Woodlake Rd., Albany, N.Y. 12203; Robert F. LeVeen, 312 Lombard St., Philadelphia, Pa. 19147; Jeannette L. Rubricius, 321 Confederate Cir., Charleston, S.C. 29407

[21] Appl. No.: 215,049

[22] Filed: Dec. 10, 1980

[51] Int. Cl.$^3$ .......... A61M 25/00

[52] U.S. Cl. .......... 604/96; 604/280

[58] Field of Search .......... 128/246, 344, 348, 349 B, 128/350 R, 276

[56] References Cited

U.S. PATENT DOCUMENTS

| | | | |
|---|---|---|---|
| 2,548,602 | 4/1951 | Greenburg | 128/4 |
| 3,395,710 | 8/1968 | Stratton et al. | 128/350 R |
| 3,797,478 | 3/1974 | Walsh et al. | 128/1 R |
| 4,141,364 | 2/1979 | Schultze | 128/349 B |
| 4,182,342 | 1/1980 | Smith | 128/348 |
| 4,248,234 | 2/1981 | Assenza et al. | 128/348 |
| 4,249,535 | 2/1981 | Hargest | 128/348 |

*Primary Examiner*—Dalton L. Truluck
*Attorney, Agent, or Firm*—John S. Hale

[57] ABSTRACT

An inflatable oral-nasal gastric tube constructed with double walls allowing the tube to be stiffened by inflation for purposes of initial placement in the patient, and deflated thereafter in order to minimize internal tissue irritation and necrosis. The tube comprises thin flexible outer and inner substantially cylindrical walls which are sealed together at their proximal and distal ends to form an inflatable structure, with a lumen defined inside the inner wall. The lumen is throughgoing and communicates with a funnel attached to the proximal end for administration of food and/or medicine and a weight is attached at the lower distal end to aid in initial placement efforts. A valve and air tube are provided on the proximal end of the tube to inject and withdraw fluid between the inner and outer walls of the tube.

8 Claims, 6 Drawing Figures

INFLATABLE GASTRIC FEEDING TUBE

BACKGROUND OF THE INVENTION

The present invention relates generally to oral-nasal gastric tubes and more specifically to a tube of variable stiffness to facilitate insertion and comfortable use thereof.

During medical treatment it is frequently necessary to force feed patients who are unable to swallow, or who must be fed continuously with a liquid nourishment substance. Some medications, such as those used in the treatment of duodenal ulcers or bleeding stomach ulcers must be introduced directly into the stomach continuously or at frequent intervals. Even if the patient is able to swallow, the schedule of medication necessitates consuming small amounts of medication at frequent intervals, thus preventing sleep and other activities.

A variety of indwelling oral-nasal gastric tubes have been developed to allow food or medication to be administered when a patient is asleep or is unable to swallow. Such tubes are normally introduced through the nose or the mouth and pushed down through the esophagus into the stomach of the patient. The tube must be relatively stiff in order to pass through the nasal and esophageal areas, but this same stiffness of the tube is uncomfortable to the patient and frequently produces complications since the tube when in use comes into contact with a surface area of sensitive internal tissue. The most common complication which arises in the use of such tubes is necrosis due to tube pressure on the nares and the larynx. Another common complication is regurgitation of acid peptic stomach contents into the esophagus. This happens because the stomach contents seep alongside the tube into the esophagus. The reflux of stomach contents produces a severe esophagitis which can cause stricture or perforation of the esophagus.

U.S. Pat. No. 4,114,625 discloses a balloon gastric tube in which the balloon is inflated to block the space around the tube where the esophagus meets the stomach. The inflated balloon prevents acid stomach contents from rising into the esophagus around the tube, and the tube itself includes at least one passageway for the passage of air in order to equalize the pressure in the stomach with the atmosphere surrounding the patient. Other references utilizing balloons are disclosed in the intubation device of U.S. Pat. No. 4,166,468 and the nasogastric catheter of U.S. Pat. No. 4,180,076.

U.S. Pat. No. 2,498,692 discloses a steerable gastrointestinal tube. The tube may be directed during insertion by pulling either one of two wires mounted on opposite sides of the tube. When a wire is pulled, the tip of the tube turns toward the wire.

None of the patents mentioned above address the problem of unnecessary tube stiffness after insertion is completed. U.S. Pat. No. 4,182,342 discloses a gastric tube comprising a semi-rigid flexible feeding tube left behind after the removal of the insertion tube. The portion of the insertion tube which remains outside of the body during insertion includes a large container for a coiled portion of the feeding tube. The feeding tube extends from the container through the insertion tube and the end of the feeding tube which extends just beyond the end of the insertion tube is enlarged so that it cannot pass back through the insertion tube. The end of the feeding tube within the container is also enlarged so that it cannot pass beyond the container. In use, the insertion tube is inserted and then is pressurized to force the coiled feeding tube through the insertion tube and into the stomach. The insertion tube is then removed, leaving the feeding tube in place. The feeding tube can then be severed from the insertion tube and used for medication and feeding. However, the device features serious drawbacks in that it requires a number of passes through the esophagus in order to install the feeding tube, and the feeding tube is necessarily of relatively small diameter in order to fit within the insertion tube. Also, the rigidity of the insertion tube is fixed.

Thus, it can be seen that there is a need in the art for an oral-nasal gastric tube of variable stiffness in order to facilitate insertion and thereafter minimize patient discomfort and complications and which also reduces the number of passes through the esophagus which are needed to install the device.

SUMMARY OF THE INVENTION

The present invention makes it possible to utilize a thin flexible tube to instill fluids into the stomach without the complications and discomfort of semi-rigid thick plastic or rubber tubes. Because the tube is inflatable it can be stiffened to facilitate easy and safe introduction.

The present invention comprises a double walled tubing using thin flexible film walls which are closed at both ends. The outer wall and inner wall form a space between the walls defining a chamber which can be inflated to extend the walls and make the tubing semi-rigid during introduction. The inner wall defines a central lumen which acts as the conduit for food and/or medication. The upper or proximal end of the tubing structure has a funnel member secured thereto which communicates with the central lumen while the lower or distal part of the tubing structure is weighted with a ring-shaped member which allows the tube to be easily extended through the throat or nose of the patient. The tubing is inflated in order to stiffen it for insertion in the patient through the use of the syringe which is inserted into a valve which communicates with the chamber and is in turn deflated with the syringe to enlarge the lumen for passage of medication and food. When the tubing is deflated, it leaves a soft flexible film on the back of the throat or through the nose which will not cause injury or discomfort to the patient while still enabling maintenance of the tube in the esophagus and reducing the risks of necrosis and damage from stomach contents. The proximal end of the tubing remains outside of the patient while the distal end of the tube remains inside the patient.

These and other objects showing the advantage of the invention will become more readily apparent when the following detailed description is read in conjunction with accompanying drawings.

DETAILED DESCRIPTION OF THE DRAWINGS

Figure 2:
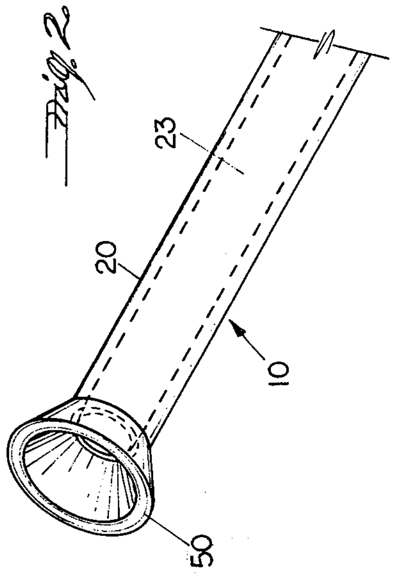
FIG. 2 is a partial perspective view of the invention when deflated for medication.
Figure 1:
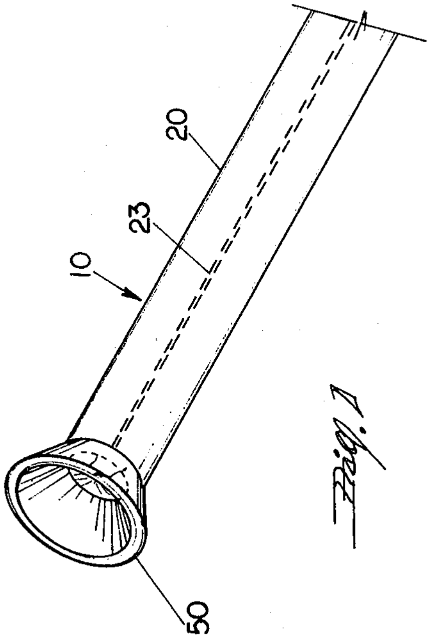
FIG. 1 is a partial perspective view of the invention when inflated for insertion.

The preferred embodiment and best mode of the invention is illustrated in FIGS. 1 through 6.

Referring generally to FIGS. 1 through 4, the gastric tubing device is generally indicated at 10. The tubing device 10 comprises a hollow or toroidal double walled tubing 20 which is inflatable, a lumen or passage 30 defined by the inner wall of the tubing, an air tube 21, and a valve 40 mounted on the air tube for inflation and deflation of the tubing 20. Tubing 20 comprises a flexible outer wall 22 and a flexible inner wall 24. Each wall is preferably constructed of an air impervious biologically inert plastic film material and can optionally be elastic in nature. Examples of film that can be used for the walls are polypropylene, polyethylene, silicon polymers or natural and synthetic latex. However, any medically suitable material can be used which has the desired medical and material characteristics required. Tubing 20 terminates at an upper or proximal end 26 and a lower or distal end 28 at which point walls 22 and 24 are sealed together to define an airtight inflatable chamber 23 therebetween. The inner surface of inner wall 24 defines lumen 30. Since the lumen 30 is not used during the typical insertion procedure, inflation of tube 20 for insertion purposes may cause inner wall 24 of tubing 20 to expand to collapse and close lumen 30.

A valve 40 is placed on an air tube 21 integrally formed on the outer wall 22 generally adjacent the upper proximate end 26 of the tube 20. The valve 40 can be a conventional releasable check valve or constructed of a material which will self-seal upon removal of a syringe which permits the tubing to be inflated or deflated by employing a syringe or the like. In view of the fact that the valve means 40 for introducing and exhausting air from tube 21 is conventional, no further description is deemed necessary. While air is envisioned as being the preferred usage, in some instances, liquid such as water or a weak aqueous solution could be used. The air tube 21 communicates with chamber 23 and seals chamber 23 from contact with the atmosphere through valve 40. Proximal end 26 remains outside of the patient during tube insertion and use.

Figure 3:
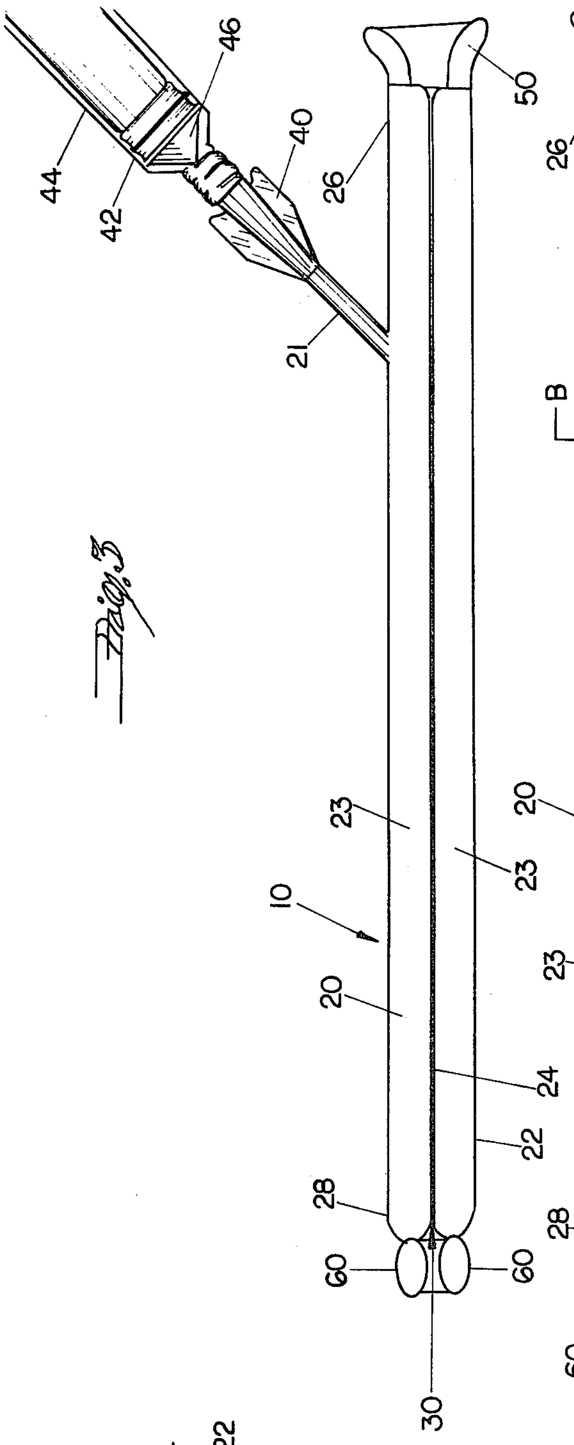
FIG. 3 is a cut-away view of the invention when inflated by a syringe for insertion.
Figure 4:
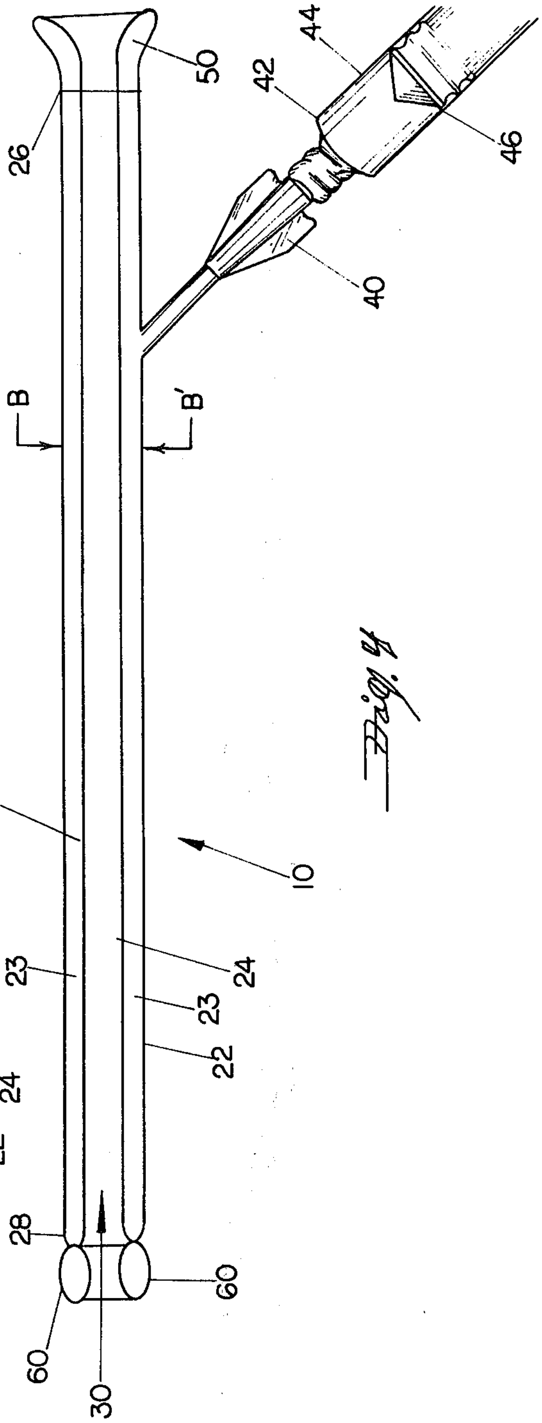
FIG. 4 is a cut-away view of the invention when deflated by a syringe for medication.
Figure 5:
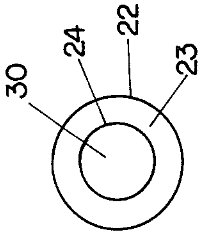
FIG. 5 is a cross-sectional view of the invention taken along B—B' of FIG. 4.

The valve 40 may be adapted to accommodate any conventional inflation means and in FIGS. 3 and 4 is shown in operative connection with syringe 42 for purposes of illustration only. Syringe 42 comprises a barrel 44 and a plunger 46 within barrel 44. The plunger 46 may be moved through the barrel 44 by the treating physician in order to inject or withdraw fluid through valve 40. FIG. 5 is a cross-sectional view of the partially deflated tubing 20 of FIG. 4, illustrating a lumen 30 of relatively large diameter which is defined by inner wall 24 of tubing 20.

Referring again to FIGS. 3 and 4, the proximal end 26 of tubing 20 is secured to and capped with a small funnel member 50 which can be constructed of a rigid or pliable plastic, to aid in administration of medication and food when the tubing 20 is placed in a patient. The distal end 28 of tubing 20 is capped with a small weighted ring 60. The weighted ring 60 helps during insertion into a patient and prevents the distal end 28 from binding against any small obstacle in the esophagus or other small passages. The ring 60 is preferably a malleable ring-shaped bag containing a heavy fluid, rather than a solid form which could block narrow passages. In one embodiment the tube is weighted at its tip by the inclusion of a small amount of mercury which is sealed off so that it does not communicate with body tissues. The ring-shaped member can also utilize any other heavy fluid or powdered metal such as iron or tungsten.

Figure 6:
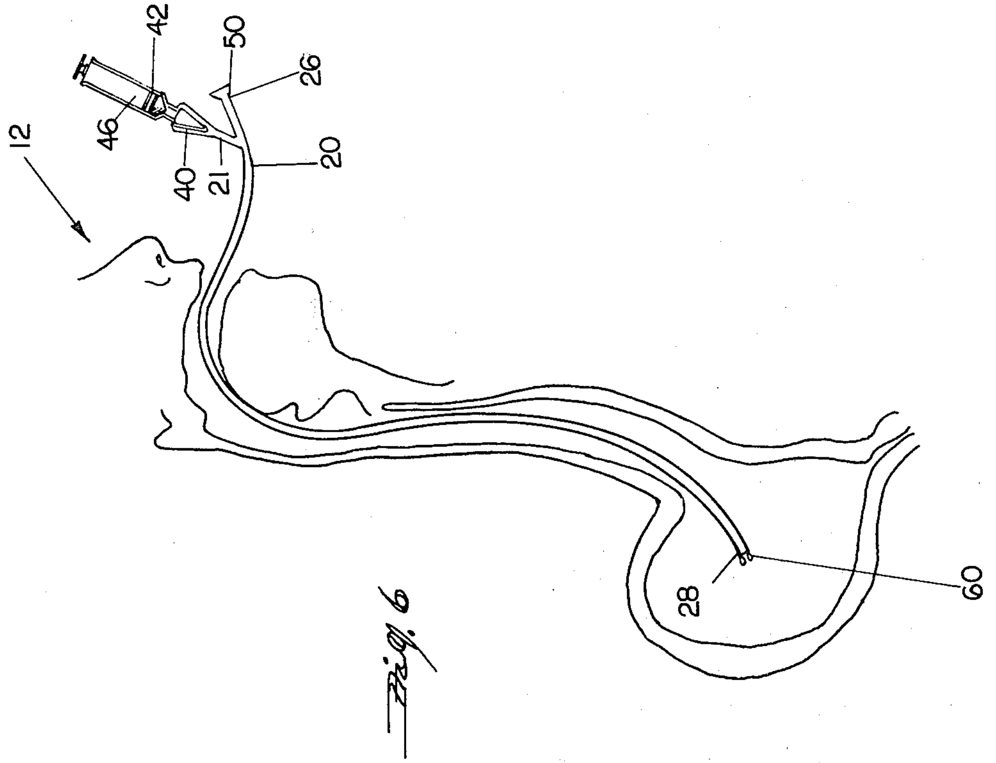
FIG. 6 is a cut-away view of the invention when inserted in a human patient.

In FIG. 6, the tubing 20 is shown after the completion of insertion into a patient 12. The proximal end 26, air tube 21, valve 40, and funnel member 50 remain outside of the patient and the tubing structure 20 is of sufficient length so that the distal end 28 and weighted ring 60 extend to the stomach of the patient 12 as shown or alternatively, to other internal areas to be treated. If desired a lubricant can be applied to the external surface of the outer wall 24 to aid the passage of the tubing into the desired body areas. The plunger 46 of syringe 42 is fully depressed so that the fluid in the syringe is deposited in chamber 23 fully inflating tubing 20. In order to administer materials through tubing 20, the plunger should be sufficiently extended withdrawing fluid so that the tubing 20 will be deflated and lumen 30 will open.

The materials chosen to manufacture the tubing walls and ring 60 should, of course, resist chemical degradation associated with activity in the stomach area, as well as be compatible with the tissues with which the tubing will come into contact. The material for the tubing should also accommodate the inflation and deflation of the tube as well as any increase and decrease in stiffness and opening and closing of the lumen 30.

Having disclosed and described the preferred embodiment of the present invention, it should be understood that the invention is not limited to the particular constructions disclosed and illustrated herein, but embrace all modified forms thereof as may come within the scope of the following appended claims.

What is claimed is:

1. An oral-nasal gastric tubing apparatus comprising a flexible, cylindrical double walled tubing being of sufficient length for insertion through the nasal cavity of a patient and into the stomach of said patient, said double walled tubing being formed by inner and outer flexible concentric cylindrical walls, said inner wall of said tubing being expandible, said outer wall of said tubing being substantially non-expandible, said walls defining an inflation space therebetween, said inner wall surrounding and defining a throughgoing lumen, said walls being sealed together at proximal and distal ends of said tubing with said lumen being open at said proximal and distal ends; valve means connected to said outer wall adjacent said proximal end and providing means for communicating with said inflation space, said valve means being adapted to receive inflation means, said distal end of said tubing being provided with weighted means to ease insertion of the tubing into a patient, said proximal end being provided with a funnel-shaped feed member allowing materials to be easily deposited within said lumen.

2. An oral-nasal gastric tubing as claimed in claim 1 wherein said weighted means comprises a sealed malleable bag defining an aperture and containing a heavy fluid and said feed member is a rigid funnel.

3. The apparatus of claim 1 wherein said weighted means comprises a ring member which is hollow and contains a heavy liquid.

4. The apparatus of claim 3 wherein said heavy liquid is mercury.

5. The apparatus of claim 1 wherein said weighted means defines a chamber containing powdered metal.

6. The apparatus of claim 1 wherein said tubing is made of plastic.

7. The apparatus of claim 1 wherein said tubing is made of rubber.

8. The apparatus of claim 1 wherein said weighted means defines a sealed malleable bag containing a heavy fluid.

* * * * *